United States Patent [19]

Mavinkurve

[11] Patent Number: 4,911,701
[45] Date of Patent: Mar. 27, 1990

[54] SANITARY NAPKIN HAVING ELASTIC SHAPING MEANS

[75] Inventor: Pramod Mavinkurve, Dendall Park, N.J.

[73] Assignee: McNeil-PPC, Inc., Milltown, N.J.

[21] Appl. No.: 160,966

[22] Filed: Feb. 26, 1988

[51] Int. Cl.⁴ .............................................. A61F 13/16
[52] U.S. Cl. .................. 604/385.2; 604/386; 604/387
[58] Field of Search ............... 604/385.1, 382.12, 386, 604/397, 398, 387

[56] References Cited

U.S. PATENT DOCUMENTS

| | | | |
|---|---|---|---|
| 4,044,769 | 8/1977 | Papajohn | 604/385.2 |
| 4,323,070 | 4/1982 | Ternstrom et al. | 604/385.2 |
| 4,425,130 | 1/1984 | Des Merais | 604/385.2 |
| 4,673,403 | 6/1987 | Lassen et al. | 604/385.1 |
| 4,692,163 | 9/1987 | Widlund et al. | 604/385.2 |
| 4,701,177 | 10/1987 | Ellis et al. | 604/379 |

FOREIGN PATENT DOCUMENTS 0155515 9/1985 European Pat. Off. ......... 604/385.1

*Primary Examiner*—C. Fred Rosenbaum
*Assistant Examiner*—Mark O. Polutta

[57] ABSTRACT

Sanitary Napkins are disclosed having elastic means for providing a greater convex shape to the body-facing portion of the central absorbent and for enabling adhesive-free placement of the flaps of a winged napkin embodiment. The elastic means comprise one or more elastic strips disposed in tension across the transverse width of the napkin to exert compressive forces on the central absorbent element and cause the flaps to fold naturally inward on the undergarment facing side. Also disclosed is a winged napkin having longitudinally disposed elastic means in one or both wings to impart a concave shape to the undergarment facing side of the wings.

17 Claims, 3 Drawing Sheets

SANITARY NAPKIN HAVING ELASTIC SHAPING MEANS

FIELD OF THE INVENTION

This invention relates to protective, absorbent liners for undergarments and more particularly, to a method for shaping sanitary napkins to fold side panels around the edges of a crotch portion of a panty and to configure the central absorbent.

BACKGROUND OF THE INVENTION

Traditionally, sanitary napkins have included a central absorbent element having a body facing side, a garment facing side, longitudinally extending sides and transverse ends. These napkins generally include an absorbent core made of loosely associated hydrophilic materials such as wood pulp, as generally known in the art. This core can be easily deformed under a relatively nominal compressive force, resulting in surface distortion and loss of good body contact.

In an effort to overcome the loss of protection due to the lack of close contact with the body of the wearer, the art has introduced absorbent products having elastic members disposed longitudinally, along the sides of the product, to create raised edge portions adjacent the central absorbent area to act as barriers against lateral leakage. See McFarland, U.S. Pat. No. 4,579,556; Widlund, et al., EPO No. 0091412, filed March 17, 1983; and Mokry, EPO No. 0155515, filed Feb. 2, 1985. Although not related to sanitary napkins, Shikata, et al., U.S. Pat. No. 4,661,102, discloses a disposable diaper having crotch tensioning means disposed to impose outward lateral tension on the crotch portion of the diaper when in use. The object of the tensioning means is to improve the aesthetic fit on the wearer and improve containment of voided materials.

Recent napkin designs address the side edge leakage problem by including side panels, flaps or wings that extend laterally from the longitudinal sides of the central absorbent. See Mattingly, U.S. Pat. No. 4,608,047, McNair, U.S. Pat. No. 4,285,343. These products are designed to protect the undergarments of their users by wrapping around the edge of undergarment. The flaps preferably have adhesive disposed on their body fluid impervious surfaces for attaching them to the underside surface of the crotch portion of the garments.

Accordingly, a need exists for a sanitary napkin that maintains close contact with the body of the wearer during normal use. There is also a need for a sanitary napkin having panty protecting flaps which can be adhered to and removed from the panty more conveniently.

SUMMARY OF THE INVENTION

A sanitary napkin is provided having elastic means for configuring the napkin. In one embodiment, the elastic means of this invention is disposed transversely across the width of the central absorbent to impart a more convex shape to the napkin's body facing side. In a second embodiment, the eleastic means is disposed within the flaps of a winged sanitary napkin for configuring the flaps to fold naturally around the sides of the crotch portion of an undergarment. Preferably the elastic means of this invention is disposed in tension and exerts a compressive force on specific sections of the napkin.

When the elastic means of this invention is disposed in the flaps to fold them over the sides of the panty crotch, the adhesive means, conventionally applied to the flaps, can be eliminated. The advantage of this construction is that the user does not have to adhesively attach the flaps to the undergarment or experience the attendant inconvenience in order to assure correct positioning of the flaps. In the preferred design, the flaps are preformed to wrap around the panty by the addition of elastic strips which can be stretched and secured without adhesive to adapt to various panty sizes.

In addition to the above features, the sanitary napkin of this invention provides for greatly facilitated removal after use. Present winged sanitary napkins require the user to face each flap by separating the adhesive from the underside of the crotch before removing the napkin from the panty crotch area. With the improved design of this invention, the user is not required to separate the flaps from the undergarment since the wings, by virtue of elastic elements, will stretch and release themselves as the user removes the napkin. It is further noted that the above improvements can be used in combination or separately to provide improved fit and/or convenient application of flaps.

it is generally known that the thin polyethylene sheets of conventional flaps are easily folded by the often elasticized undergarment. In an effort to overcome this deficiency in winged napkin designs, this invention also contemplates providing the flaps of a winged sanitary napkin with longitudinally disposed elastic means for providing a convex configuration to the body-facing side of the flaps. This design enables the flaps to resist being folded over by the undergarment when the undergarment is pulled up against the wearer.

It is, therefore, an object of this invention to provide a winged sanitary napkin that is easier to remove after use.

It is another object of this invention to provide a sanitary napkin that creates a naturally convex shape of the central absorbent for a closer fit to the body of the wearer.

it is still another object of this invention to provide a winged sanitary napkin having elastic means in the flap or wing area to provide a configuration which enables an adhesive-free placement of the flaps around the sides of the crotch portion of the panty.

With these and other objects in view, which will become apparent to one skilled in the art as the description proceeds, this invention resides in the novel construction, combination, arrangement of parts and methods substantially as hereinafter described and more particularly defined in the attached claims.

DESCRIPTION OF THE INVENTION

Figure 1:
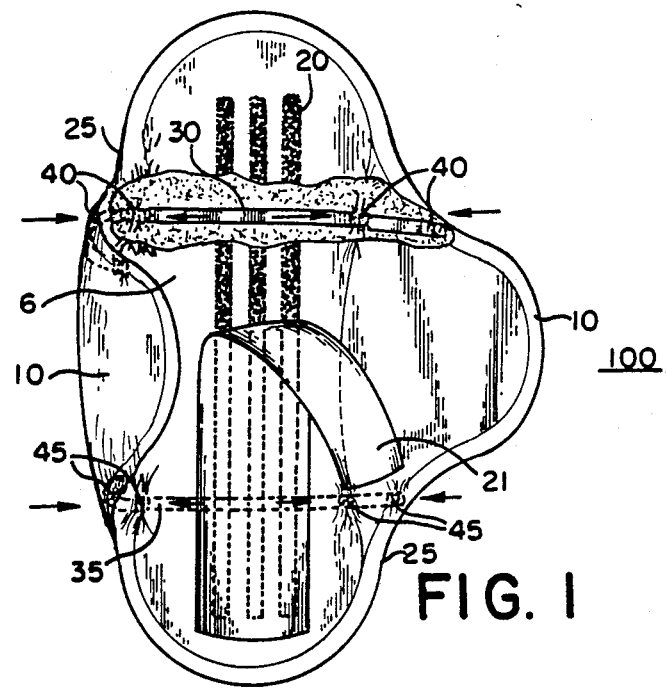
FIG. 1: is a planar view of the undergarment facing side of a winged sanitary napkin illustrating a partially segmented view of one elastic means and the resulting configuration of one flap.
Figure 2:
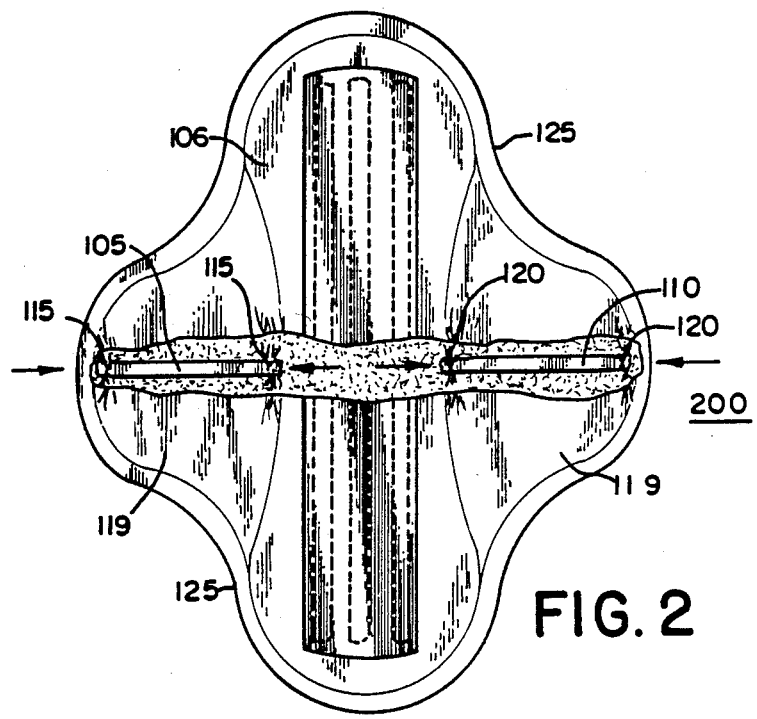
FIG. 2: is a planar view of the undergarment facing side of another winged sanitary napkin illustrating a partially segmented view of an elastic means disposed substantially within the flap members.
Figure 3:
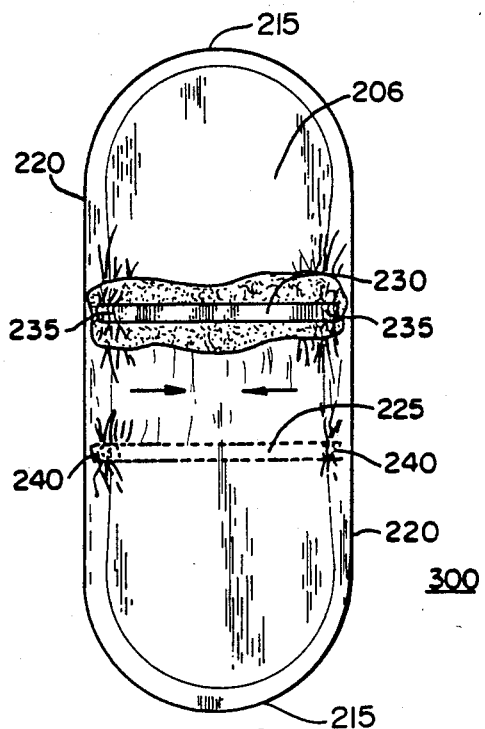
FIG. 3: is a top planar view of another sanitary napkin illustrating a partially segmented view of elastic means for configuring the central absorbent core of the napkin.

With reference to the drawings, and particularly FIGS. 1-3 thereof, there are shown preferred sanitary napkins 100, 200 and 300 having elastic means disposed therein for providing a more convex shape to the body-facing side and/or for configuring the flaps to fold over a side of a crotch portion of an undergarment.

Figure 5:
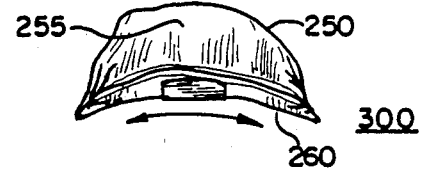
FIG. 5: is a transverse end view of the napkin of FIG. 3 illustrating the resulting configuration of the central absorbent.

With respect to FIGS. 3 and 5, a sanitary napkin 300 is provided having an absorbent element 206 including longitudinally extending sides 220, transverse ends 215, a body-facing side 250, and an undergarment facing side 260. This napkin 300 is provided with elastic means, depicted as elastic strips 225 and 230, disposed in tension transversely across the absorbent element 206 and affixed to the napkin 300 for providing a more convex shape for the body-facing side 250. In the preferred embodiment of this configuration, the eleastic means is affixed across the absorbent element 106 at two opposing points, illustrated by napkin locations 235 and 240, on the longitudinally extending sides 220 of the napkin. In a more preferred embodiment, the elastic means is disposed adjacent a fluid impervious backing layer of the napkin to assure a tensioning force that will produce a more convex shape to the body facing side of the napkin.

Figure 4:
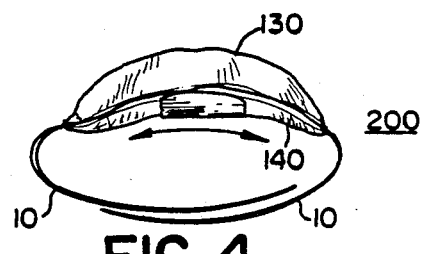
FIG. 4: is a transverse end view of the napkin of FIG. 2 illustrating the resulting configuration of the flaps.

In the embodiments as described by FIGS. 1, 2 and 4, sanitary napkins 100 and 200 are provided with elastic means within at least one of their flaps 10 and 119 for configuring the flap to fold over a side of a crotch portion of an undergarment. As described in FIG. 1, one of these napkin embodiments preferably has elastic means, illustrated as elastic strips 30 and 35, disposed within both flaps 10. In this embodiment, the elastic means is disposed transversely across the absorbent element 6 and affixed to each of the flaps 10. Preferably, the elastic means is affixed at two points lying on a line of juncture between the absorbent element 6 and the flaps 10. As illustrated in FIG. 1, these points are represented by napkin locations 40 and 45. The elastic means is preferably disposed in tension, as similarly described for the embodiment of FIG. 3, to compress the absorbent element 6.

The napkin embodiment 200 as depicted in FIG. 2, includes elastic strips 105 and 110 disposed within at least one of its flaps 119. The strips 105 and 110 are preferably affixed at one end at a point of juncture between the absorbent element 106 and said one of the flaps 119 and at the other end at a point lying on the periphery of the flap. Preferably, elastic strips 105 and 110 are disposed in tension within both of flaps 119 and affixed at points 115 and 120.

The elastic strips 30, 35, 105, 110, 225 and 230 of the above-described napkin embodiments 100, 200 and 300, are preferably stretched about 10% to 200% of their original length, preferably about 160% when secured to the napkin. Preferably, the elastic strips are positioned adjacent the fluid barrier surface and the tissue layer, pulp and body-fluid pervious surface are placed over the elastic strips before sealing. If desired, the elastic strips may be secured to the fluid barrier surface along their entire length by continuous or intermittent bonding in order to assure the application of uniform tension and avoid bunching of the barrier surface.

The absorbent elements 6, 106, and 206 of this invention, as illustrated in FIG. 1-3, should be made of soft, comfortable material. Preferably these elements are cut into an "hour glass shape", when flaps are employed, as illustrated in FIGS. 1 and 2. Adequate absorbency may be built into the core of the absorbents without adding bulk, by adding conventional super-absorbent materials such as a cross-linked acrylate polymer, which have the properties of high-liquid retention.

Generally the central absorbent elements 6, 106, and 206 are about 4-10 inches in length, preferably about 6-9 inches and comprise a core which preferably is made of loosely associated absorbent hydrophilic material such as cellulose fibers, wood pulp, regenerated cellulose or cotton fibers, and/or other absorbent materials generally known in the art.

the side of the napkin to worn against the body of the user is covered by body-fluid pervious surfaces 130 and 250 which can be any resilient, relatively non-absorbing fluid pervious material. This material is provided for comfort and conformability and directs fluid to an underlying layer, for example, wood pulp, which retains such fluid. The cover should retain little or no fluid in its structure to provide a relatively dry surface next to the skin. Generally, the fluid permeable surfaces 130 and 250 are a single, rectangular sheet of material having a width sufficient to cover the body-facing side of the absorbent elements 6, 106 and 206. Preferably, the fluid pervious surfaces 130 and 250 are longer than the core so as to form end tabs, which may be sealed with other pervious or non-pervious layers to fully enclose the cores. The fluid pervious surfaces 130 and 250 are preferably a nonwoven fabric made of fibers or filaments of thermoplastic polymers such as polyethylene or polypropylene, or an apertured polymeric film.

Underlying the core of the absorbent elements 6, 106, and 206 can be another layer of absorbent material to provide additional resiliency to the product. This additional layer can extend beyond the longitudinal sides of the absorbent core to entrap any body fluid which escapes from the sides of the absorbent elements 6, 106 and 206. This layer may be substantially wider than the core of the central absorbents 6, 106, and 206, and may extend into the flaps of a winged napkin configuration 100, 200 and 600. The absorbent layer may comprise a thin, absorbent layer of material such as a tissue, fabric or the like, made of cellulosic fibers. Because such material is provided as a safety measure and is only required to contain escape fluid, it need not be very absorbent at all and, in fact, may be comprised of any capillary or cellular system including hydrophobic material. however, the preferred material is a hydrophilic fabric comprised of cellulosic fibers such as wood pulp tissue or other suitable hydrophilic woven or non-woven material. The preferred tissue has the advantage of providing resiliency and conformability to the product.

The sanitary napkins 100, 200, 300 and 600 of this invention further include body-fluid impervious surfaces 140 and 260 on the undergarment-facing side of the absorbent elements 6, 106, and 206. The impervious surfaces 140 and 260 will preferably allow the passage of air and moisture vapor while blocking the passage of fluid to the outer surface. The impervious surfaces 140 and 260 may be heat sealed or fastened by way of adhesives to a core or to a core wrapped in a pervious surface cover. The impervious surfaces 140 and 260 may comprise any thin, flexible, body fluid impermeable material such as, a polymeric film, for example, polyethylene, polypropylene, cellophane or even a normally fluid pervious material that has been treated to be impervious, such as impregnated fluid repellent paper or nonwoven fabric material.

The preferred winged configurations of FIGS. 1 and 2 include flaps 10 and 119 which extend laterally from each of the longitudinal sides 25 and 125 of the absorbent elements 6 and 106. Although preferably not including absorbent pulp materials, these flaps 10 and 119 can include a body fluid impervious backing such as the materials described in connection with the above-mentioned body fluid impervious surfaces 140 and 260. It is also expected that the flaps 10 and 119 can comprise body fluid pervious covers, much like the above-mentioned body fluid pervious layers 130 and 250, and absorbent tissues disposed between their covers and their backings. In addition, it is preferred that the flaps 10 and 119 of this invention contain absorbent tissue with sufficient capillary action to retain small quantities of escaped liquid. This tissue can be heat sealed or adhesively sealed around the edges of the flaps 10 and 119 with the preferred impervious backings and body fluid pervious covers of the flaps 10 and 119 to form absorbing areas.

Also included with this invention are attachment adhesive elements 20 which can be made of any known pressure-sensitive adhesive material. As used herein, the term "pressure-sensitive" refers to any releasable adhesive or releasable tenacious means. Adhesive compositions suitable for sanitary napkins, include, for example, the water-based pressure-sensitive adhesives such as acrylate adhesives. Alternatively, the adhesive may comprise rapid setting thermoplastic "hot melt", rubber adhesives or two-sided adhesive tape. As is customary in the art, a coated paper release strip 21 can be applied to protect any of the adhesive elements, such as strips 20, prior to use.

Figure 6:
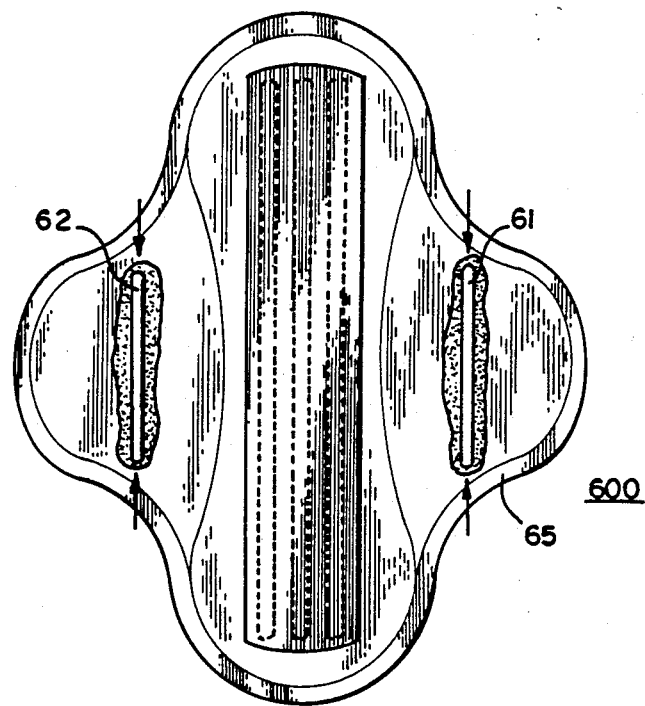
FIG. 6: is a planar view of the undergarment facing side of a winged sanitary napkin illustrating a partially segmented view of elastic means disposed longitudinally within each flap member.

Referring now to FIG. 6, a sanitary napkin embodiment 600 is illustrated having longitudinally disposed elastic means, preferably elastic strips 61 and 62, for configuring the flap to resist being folded by an undergarment. It is expected that the ends of elastic strips 61 and 62 would be disposed on the outer seam area 65 with adhesive although this is not a requirement. preferably the flaps are configured by the elastic means so that they present a concave configuration on their undergarment-facing side. This preferred configuration will provide greater resistance to buckling when the panty is raised by the wearer. Since the flaps remain extended in this configuration, they can easily extend out of the peritoneal region and thus cover the sides of the crotch portion of an undergarment to minimize failure.

From the foregoing it can be realized that this invention provides an improved sanitary napkin having an elastic member for providing a greater convex shape to body-facing portion of the napkin and/or for enabling adhesive-free placement of the flaps of a winged sanitary napkin. The elastic elements disclosed can also allow the wings to stretch and flex with the panty crotch, keeping the wings in place for better protection. The napkins of this invention are easier to remove after use, since the additional task of separating the adhesive on the flaps from the panty is eliminated.

Although various embodiment have been illustrated, this was for the purpose of describing, but not limiting the invention. Various modifications, which will become apparent to one skilled in the art, are within the scope of this invention described in the attached claims.

What is claimed is:

1. A sanitary napkin comprising:
   (a) an absorbent element having longitudinally extending sides, transverse ends, a body-facing side covered by a fluid pervious member, and an undergarment facing side covered by fluid impervious backing layer, and
   (b) an elastic strip disposed in tension transversely across said absorbent element and affixed to said napkin at at least two points to impart a convex shape toward the body of the user to said body-facing side.

2. The sanitary napkin of claim 1 wherein said elastic means is affixed to said absorbent element of said napkin at two opposing points on said longitudinally extending sides of said absorbent element.

3. The sanitary napkin of claim 1 wherein said elastic means is disposed adjacent said fluid impervious backing layer of said absorbent element.

4. The sanitary napkin of claim 1 wherein said elastic means is extended in tension from about 10% to 200% of its original length.

5. A sanitary napkin comprising:
   (a) an absorbent element having longitudinally extending sides, transverse ends, a body facing side and an undergarment facing side,
   (b) flaps extending laterally from each of said longitudinal sides of said absorbent element; and
   (c) elastic means disposed within at least one of said flaps for configuring said one of said flaps to fold over on the undergarment facing side.

6. The sanitary napkin of claim 5 wherein said elastic means comprises an elastic strip disposed within both flaps.

7. The sanitary napkin of claim 5 wherein said elastic means comprises an elastic strip disposed laterally from said absorbent element and affixed at one end at the juncture between said absorbent element and said one of said flaps, and at the other end on the periphery of said one of said flaps.

8. The sanitary napkin of claim 6 wherein said elastic means extends transversely across said absorbent element and is affixed at a point lying on the periphery of each of said flaps.

9. The sanitary napkin of claim 8 wherein said elastic means is also affixed at two points lying about on a line of juncture between said absorbent element and said flaps.

10. The sanitary napkin of claim 9 wherein the portion of said elastic means extending across said absorbent element is disposed in tension to compress said absorbent element.

11. A sanitary napkin comprising:
   (a) an absorbent element having longitudinally extending sides, transverse ends, a body facing side and an undergarment facing side;
   (b) flaps extending laterally from each of said longitudinally sides of said absorbent element;
   (c) elastic means disposed within at least one of said flaps for configuring said one of said flaps to fold over on the undergarment facing side; and
   (d) wherein said elastic means comprises two elastic strips disposed transversely across a portion of said napkin.

12. The sanitary napkin of claim 11 wherein said elastic strips are affixed in tension to compress said absorbent element.

13. The sanitary napkin of claim 12 wherein said elastic strips are disposed on said flaps and affixed in tension for configuring said flaps over the undergarment facing side of said napkin.

14. A sanitary napkin having a body facing side and an undergarment facing side comprising:
   (a) an absorbent element having longitudinally extending sides and transverse ends;
   (b) flaps extending laterally from each of said longitudinal sides of said absorbent element; and
   (c) an elastic strip disposed longitudinally within at least one of said flaps for providing a more concave shape to the undergarment-facing side of said one of said flaps and a convex shape to the body-facing side of said one of said flaps.

15. The sanitary napkin of claim 14 wherein said elastic means is disposed within both flaps.

16. The sanitary napkin of claim 15 wherein said elastic means comprises elastic strips disposed parallel to the longitudinally extending sides of said absorbent element.

17. A sanitary napkin comprising:
   (a) an absorbent element having longitudinally extending sides, transverse ends, a body-facing side covered by a fluid pervious member, and an undergarment facing side covered by fluid impervious backing layer; and
   (b) elastic means disposed in tension transversely across said absorbent element and affixed to said napkin at at least two points to impart a convex shape to said body-facing side; and
   (c) flaps extending laterally from each of said longitudinally extending sides of said absorbent element.

* * * * *